United States Patent
Smith et al.

(10) Patent No.: US 8,650,956 B2
(45) Date of Patent: Feb. 18, 2014

(54) VIBRATION TEST ARRANGEMENT

(75) Inventors: Stephen J Smith, Derby (GB); Philip D Blavins, Derby (GB); Andrew T Backler, Derby (GB)

(73) Assignee: Rolls-Royce plc, London (GB)

( * ) Notice: Subject to any disclaimer, the term of this patent is extended or adjusted under 35 U.S.C. 154(b) by 529 days.

(21) Appl. No.: 12/919,815

(22) PCT Filed: Feb. 18, 2009
(Under 37 CFR 1.47)

(86) PCT No.: PCT/GB2009/000422
§ 371 (c)(1),
(2), (4) Date: Apr. 27, 2011

(87) PCT Pub. No.: WO2009/112795
PCT Pub. Date: Sep. 17, 2009

(65) Prior Publication Data
US 2012/0152023 A1    Jun. 21, 2012

(30) Foreign Application Priority Data
Mar. 12, 2008  (GB) .................................. 0804488.5

(51) Int. Cl.
*G01N 3/32* (2006.01)
(52) U.S. Cl.
USPC .................... 73/577; 73/671; 73/812; 73/859
(58) Field of Classification Search
USPC ............ 73/577, 583, 663, 671, 860, 812, 859
See application file for complete search history.

(56) References Cited

U.S. PATENT DOCUMENTS 6,820,468 B2 * 11/2004 Powers et al. ................... 73/49.7
2011/0239774 A1 * 10/2011 Schuyler et al. ................ 73/812

FOREIGN PATENT DOCUMENTS

| GB | 545476 A | 5/1942 |
| GB | 2 287 757 A | 9/1995 |
| JP | A-2002-236074 | 8/2002 |
| JP | A-2003-270081 | 9/2003 |

OTHER PUBLICATIONS

British Search Report issued in British Patent Application No. GB0804488.5, dated Jul. 4, 2008.
Written Opinion of the International Searching Authority issued in Patent Application No. PCT/GB2009/000422, dated Sep. 3, 2010.
International Search Report issued in Patent Application No. PCT/GB2009/000422, dated Sep. 3, 2010.

* cited by examiner

*Primary Examiner* — John Chapman, Jr.
(74) *Attorney, Agent, or Firm* — Oliff PLC

(57) ABSTRACT

Vibration test arrangements incorporate an isolation device. In order to allow the isolation device to operate on one side only of a component subject to vibration testing a clamp association is provided between isolation elements. An abutment pressure to retain and present the component is generated between the isolation elements utilizing the clamp association and an appropriate displacement mechanism. The displacement mechanism is controlled by a controller in a control loop incorporating a sensor to determine operational characteristics of the arrangement and appropriate drivers for the displacement mechanism.

19 Claims, 2 Drawing Sheets

VIBRATION TEST ARRANGEMENT

BACKGROUND

The present invention relates to vibration test arrangements and more particularly vibration test arrangements utilised with regard to components such as aerofoils utilised in rotors of a gas turbine engine.

It will be understood that a large number of components require testing to determine their performance in use. One form of testing is fatigue testing and in particular high cycle vibration fatigue testing. With respect to some components such as low pressure compressor blades, eg fan blades, in gas turbine engines their size and thus motions during testing can be severe. It is known to provide isolator devices to assist with respect to high cycle vibration fatigue testing of components and particularly with respect to components having an aerofoil shape. An aerofoil is held in a specific fixture and can be excited in a number of ways and in a particular mode of vibration. Any mode of vibration higher than the first fundamental mode will have node lines which are stationary when the vibration mode is excited. The isolator device is used to inhibit other modes of vibration and isolate the mode of vibration of interest by resting against the node line on the aerofoil so causing that part of the aerofoil to be stationary encouraging the mode of vibration of interest to be excited when the method of excitation is switched on.

FIG. 4 illustrates a typical prior test arrangement 1 for an aerofoil 2 of a blade component. Two isolator devices 3, 4 are located upon a node line 5 of a mode of vibration of interest. As indicated above the isolation devices 3, 4 are presented upon the node line 5 in order to isolate the mode of vibration of interest. The prior isolation devices 3, 4 act against parts of the aerofoil 2 and must absorb relatively large values of vibration energy as well as untwisting actions along the node line 5 during motion of the aerofoil 2. As indicated above the aerofoil 2 is generally a low pressure compressor blade, eg a fan blade from a gas turbine engine. The isolation devices 3, 4 comprise an elastomeric and typically rubber element having a cut edge or point to engage the aerofoil 2. The elastomeric element is held in a rigid clamp for presentation to the aerofoil 2.

SUMMARY

By providing isolation devices 3, 4 which are rigid in nature it will be understood that there is generally a rapid wear of the rubber tip in engagement with the aerofoil 2. Such rapid wear results in instability in the mode of vibration and therefore a potential necessity to abort a test before full duration of a test cycle has been achieved. It will also be understood that test set up times can be lengthy due to the requirement to locate both isolation devices 3, 4 through their isolator element edges in alignment with the node line 5.

An alternative approach might be to present an isolation device to one side only of a component such as an aerofoil 2. In such circumstances, the component may be effectively retained and clamped by the isolation device. However, in such circumstances, control of the necessary isolation conditions would still be required.

Prior isolation devices utilised in vibration test arrangements have limitations.

In accordance with aspects of the present invention there is provided a vibration test arrangement for a component, the arrangement comprises an isolation device having a first isolation member and a second isolation member, the first isolation member and the second isolation member mounted with a clamp association to provide an isolation abutment pressure between the first isolation member and the second isolation member, the clamp association comprising a displacement mechanism to provide relative displacement between the first isolation member and the second isolation member, the displacement mechanism associated with a controller and the controller associated with a sensor to determine the isolation abutment pressure, the sensor providing signals to the displacement mechanism to alter the isolation abutment pressure.

Also in accordance with aspects of the present invention there is provided an isolation device for a vibration test arrangement, the device having a first isolation member and a second isolation member, the first isolation member and the second isolation member mounted with a clamp association to present an isolation abutment pressure between the first isolation member and the second isolation member, the clamp association comprising a displacement mechanism to provide relative displacement between the first isolation member and the second isolation member, the displacement mechanism associated with a controller and the controller associated with a sensor to determine the isolation abutment pressure, the sensor providing signals to the displacement mechanism to alter the isolation abutment pressure.

Typically, the displacement mechanism comprises a motor associated with the first isolation member and the second isolation member through a cam and/or gear. Generally, the clamp association presents the first isolation member and the second isolation member substantially aligned with each other. Normally, the displacement mechanism is arranged to provide displacement along a common axis between the first isolation member and the second isolation member.

Typically, the clamp association includes a spring.

Typically, one or each of the isolation members is provided in an aperture, the aperture configured to allow lateral movement relative to an axis between the isolation members. Typically, the aperture has a size greater than the isolation member. Possibly, the aperture is formed from material arranged to allow deformation of the aperture about the isolation member.

Normally, the first isolation member is provided on a first arm and the second isolation member is provided on a second arm. Generally, the first arm and the second arm are arranged on a post. Generally, the first arm and the second arm are presented about the same post. Generally, the first arm and the second arm are substantially parallel to each other. Generally, the clamp association is arranged on the post. Generally, the spring is associated with the post. Possibly, a guide post is provided to ensure retention of orientation of the arms.

Generally, the isolation abutment pressure is arranged to be sufficient to clamp the component. Typically, the component is an aerofoil. Generally, the aerofoil is part of a gas turbine engine compressor blade or part of a gas turbine engine fan blade. Generally, there are means to vibrate the component and means to hold an end of the component.

BRIEF DESCRIPTION OF THE DRAWINGS

Various exemplary aspects will be described with reference to the drawings, wherein.

DETAILED DESCRIPTION OF THE EMBODIMENTS

Figure 4:
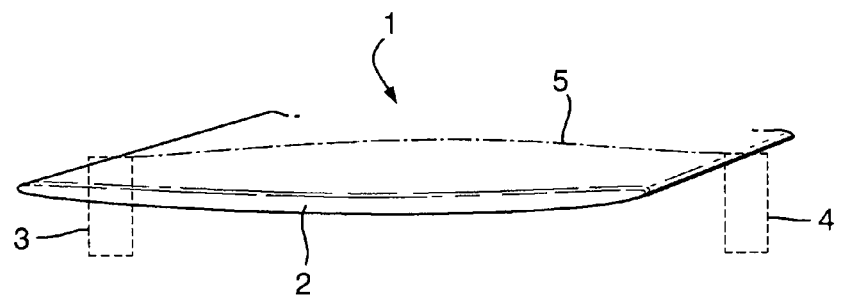
FIG. 4 is a view of a prior test arrangement.
Figure 1:
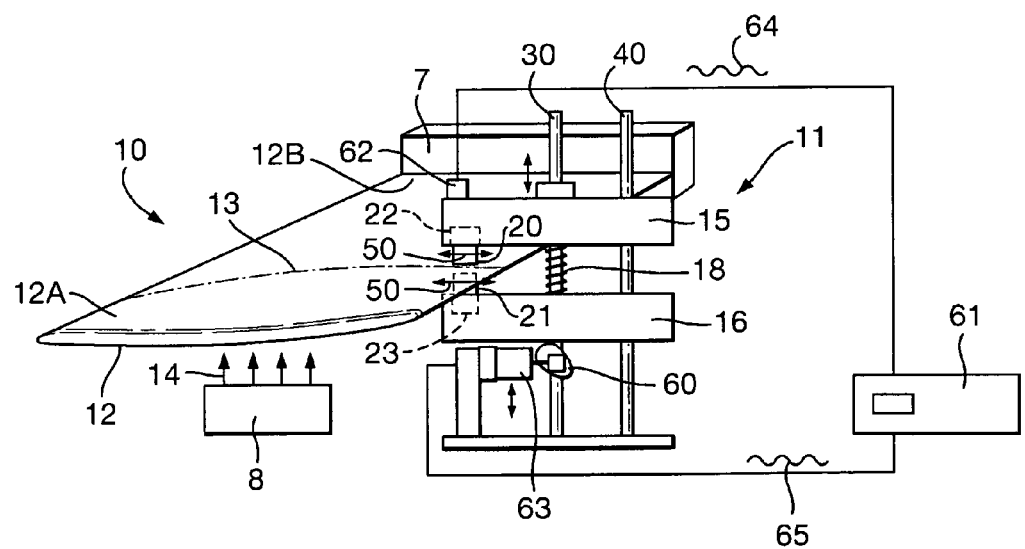
FIG. 1 is a schematic side view of a vibration test arrangement.

Embodiments and aspects of the present invention will now be described by way of example and reference to the accompanying drawing shown as FIG. 1 depicted a schematic side view of a vibration test arrangement in accordance with aspects of the present invention.

As indicated previously provision of rigid isolation elements in the form of cut rubber components at each side of an aerofoil such as a compressor blade, or a fan blade, results in problems with regard to premature wear and potentially spurious results. By aspects of the present invention an isolation device is provided to isolate a vibration mode of interest through engagement to one side only of a component such as an aerofoil.

Referring to FIG. 1 providing a schematic side illustration of a vibration test arrangement in accordance with aspects of the present invention. The arrangement 10 has an isolation device 11 associated with one side or edge of a component 12 about a node line 13 of a desired mode of vibration of interest. Vibration of the component 12 is typically through an appropriate mechanism 8 schematically illustrated by arrowheads 14. The arrowheads 14 indicate the high velocity gas, or air, jets which are directed onto the component from the mechanism 8. It will be noted that in comparison with prior arrangements that the isolation device 11 only acts upon one side of the component 12. This component 12 as illustrated is an aerofoil of a compressor blade, e.g. a fan blade, taken from a gas turbine engine. It is to be noted that a first end 12B of the component 12 is held rigidly in a fixture 7, in the case of an aerofoil of a blade, this is the root of the blade. A second end 12A is unrestrained and free to vibrate.

The isolation device 11 comprises a first arm 15 and a second arm 16. A clamp association 18 provides an appropriate isolation abutment force between isolation elements 20, 21 presented towards ends of the arms 15, 16. This isolation abutment force retains the component 12 in position.

Isolation elements 20, 21 are located and presented from the arms 15, 16 in an axial clamping movement, that is to say substantially in the direction of the clamping association 18. As will be described later, lateral movement relative to the axial direction and in the direction of the arrowheads 50 is advantageously allowed by the nature of the association between the isolation elements 20, 21 in their respective arms 15, 16. In engagement with the component 12 the axial and lateral movements of the isolation elements 20, 21 will ensure reduced wear and therefore generally give an extended operational life in comparison with prior rigidly presented isolation elements.

In order to appropriately present the isolation elements 20, 21 to engage the component 12 about the node line 13, the association 18 generates an isolation abutment pressure or force between the elements 20, 21.

As indicated above generally the isolation elements 20, 21 will be formed from rubber or an appropriate elastomeric material. The isolation elements 20, 21 will be shaped to have an edge to provide focus with regard to engagement along the node line 13.

Figure 2:
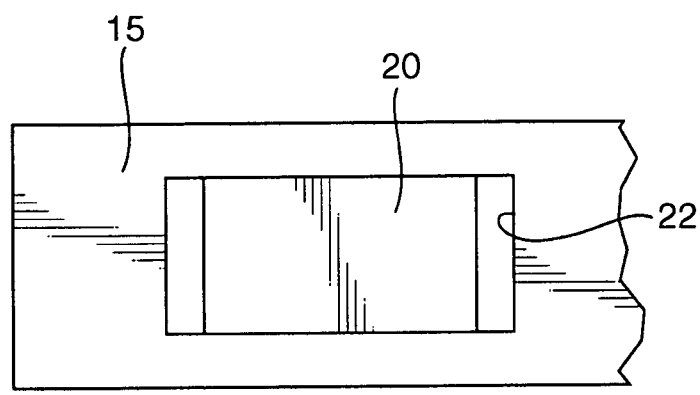
FIG. 2 is an enlarged view of an aperture.
Figure 3:
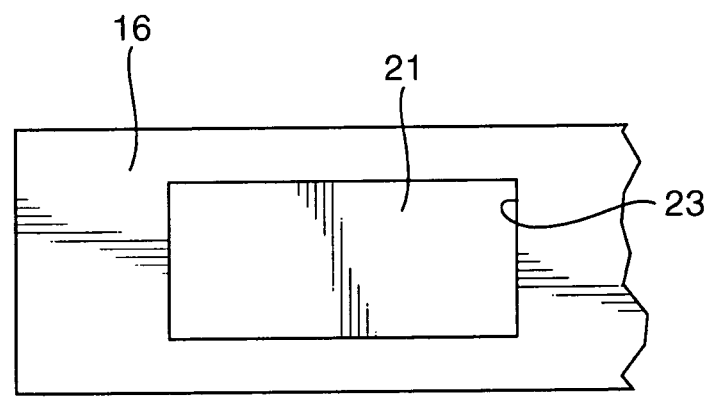
FIG. 3 is an enlarged view of another aperture.

In order to achieve the lateral movement in the direction of arrowheads 50 the isolation elements 20, 21 will be positioned in apertures 22, 23 within the arms 15, 16. Lateral movement in the direction of arrowheads 50 may be achieved through providing respective 22 (FIG. 2) which are slightly oversized for the elements 20, 21. In such circumstances there will be a gap between sides of the elements 20, 21 and its aperture 22 to allow the lateral movement in the direction of arrowheads 50. Alternatively, the apertures 23 (FIG. 3) may be formed from or at least have about the side of the apertures 23 a material which may be deformed when loaded through the elements 20, 21 again to allow lateral movement in the direction of arrowheads 50.

Generally, the isolation elements 20, 21 will be loose within the apertures 22, 23 of the arms 15, 16 presenting them to the component 12. In such circumstances the elements 20, 21 can be readily removed when required and replaced with new elements for further test procedures or if worn or a different isolation member configuration is required particularly with regard to enabling the engagement edge to align with the node line 13.

It will be understood that by arranging the isolation device 11 along one side only of the component 12 there is a reduction in set up times with regard to test procedures in that it is only necessary to align the device 11 through the elements 20, 21 with the node line 13 at that side. Furthermore, by providing the elements 20, 21 as loose fittings or otherwise within mountings of the arms 15, 16 there will be a reduction in wear rate upon on the tip edges of the elements 20, 21. Such reductions in wear will prevent early degradation and necessary shutdown of fatigue test vibration operations when wear to the elements 20, 21 is such that other modes of vibration may be excited.

The isolation abutment pressure is generated between the elements 20, 21 upon the component 12 along the node line 13. This isolation abutment pressure is generated through the association 18 subject to appropriate adjustment through the displacement mechanism 60. The association 18 generally provides for axial displacement of the elements 20, 21 along an axis of alignment to generate respective axial pressure to engage and clamp a side of the component 12 with an isolation abutment pressure.

It is preferred as illustrated in FIG. 1 that the arms 15, 16 are presented substantially parallel on two poles 30, 40 in order to generate stability in a parallel orientation. It will be understood that presenting the arms 15, 16 on a single pole may lead to tilting or otherwise out of the desired parallel orientation. In such circumstances the arms 15, 16 will have respective close tolerance holes or apertures to accommodate the poles 30, 40. Holes will be drilled or otherwise formed in the arms 15, 16 to accommodate each pole 30, 40 with at least a spring engaging about those holes to facilitate the necessary isolation abutment pressure. The spring will inhibit bounce back as the displacement mechanism 60 operates and also will allow some axial movement in addition to lateral movement 50 as the component 12 vibrates. The spring facilitates a double indirect loading aspect to the presentation of the elements 20, 21 to allow the axial displacement as described as result of vibration loading to the component 12.

As can be seen the arms 15, 16 are generally robust and stable elements to ensure rigidity in presentation of the elements 20, 21 in terms of orientation. However, as indicated above the arms 15, 16 incorporate appropriate mountings typically in the form of apertures 22, 23 in which the elements 20, 21 are located. These mountings will allow the lateral movement in the direction of arrowheads 50 whilst axial movement is allowed through compression and extension of the spring. The elements are typically aligned on a common axis.

There are advantages with regard to aspects of the present invention in relation to reducing set up time in that the isolation device 11 is only presented to one side of the component, that is to say the aerofoil blade 12. Furthermore, by reduced wear upon the isolation elements 20, 21 it will be understood that these elements will require less replacement in use and it may be that isolation members may last for up to ten times longer compared to prior isolation members. Additionally, by having greater durability with regard to the isolation elements 20, 21 the vibration test arrangements can more predictably operate for a full test cycle avoiding the necessity for premature aborting of testing prior to completion of all the desirable test cycles.

The isolation elements are positioned in accordance with aspects of the present invention by the clamp association but, effectively float upon the spring association as well as within the mountings provided by the apertures in the arms reducing rigidity and therefore wear as indicated above. The isolation members are effectively presented only to one side of the test component and clamped with the isolation abutment pressure. Engagement with the isolation elements aids and reduces the complexity of presenting the isolation device upon a node line of the desired mode of vibration for testing. The isolation elements are spring loaded and advantageously spring tension can be adjusted. In such circumstances less wear should be presented to the isolation device and in particular the isolation elements in accordance with aspects of the present invention.

As indicated above particular aspects of the present invention relate to the capability of retaining and presenting a component 12 through use of an isolation device 11 to only one side of the component 12. In such circumstances, the isolation device 11 through the clamping association 18 must generate sufficient isolation abutment force to retain the component 12. This is achieved through the displacement mechanism 60 displacing the isolation elements 20, 21 towards and away from each other along a notional axis of alignment. In the embodiment depicted the elements 20, 21 are presented through robust and substantially rigid arms 15, 16. It will be appreciated that the use of arm 15, 16 has particular advantages in terms particularly of retaining relative position between the elements 20, 21 in a simple mechanical arrangement. However, alternative arrangements may be provided.

Within the isolation device 11 in accordance with aspects of the present invention typically the displacement mechanism comprises as illustrated a pole or rod 30, 40 upon which the arms 15, 16 are presented. Generally as illustrated a spring or spring like member is provided between the arms 16, 17 to provide for robust presentation of the element 20, 21. It will be appreciated that a spring will act to dampen bounce back or other factors due to movement of the displacement mechanism 60. It will also be understood that the spring will allow some axial movement as a result of vibration induced movements within the component 12.

The purpose of the clamp association 18 is to generate the abutment pressure between the elements 20, 21. This as indicated is achieved by displacement. The displacement mechanism 60 as illustrated generally comprises a gear and/or cam association with the arms 15, 16 in order to move these arms axially, that is to say upwards and downwards along the pole or rod 30, 40 in order to generate the abutment pressure between the elements 20, 21. Of particular advantage with regard to aspects of the present invention is that the abutment pressure can be adjusted by operating the displacement mechanism utilising an appropriate control system.

In a simple mode of operation the displacement mechanism 60 will be operated until an appropriate abutment pressure is achieved through the elements 20, 21 against the node line 13. Once the appropriate isolation of the mode of vibration of interest has been achieved further displacement and therefore increase in abutment pressure will no longer be required. The displacement mechanism in such circumstances would simply retain that abutment pressure. However, in a practical situation not all of the component 12 will be subject to vibration and therefore for a number of reasons active control of the abutment pressure would be advantageous. As indicated above it is possible that the isolation elements 20, 21 may wear reducing engagement edges or points with the component 12 or with a curved component such as an aerofoil the point of engagement along the curve of the aerofoil may change non-linearly and so altering the abutment pressure presented through the elements 20, 21. In such circumstances active adjustment of the abutment pressure is advantageous.

FIG. 1 provides illustration of a simple feedback loop controller arrangement for utilisation in accordance with aspects of the present invention.

In order to achieve control a controller 61 is connected to both a sensor 62 and a drive element 63 for the displacement mechanism 60. The sensor 62 which may take the form of an accelerometer forwards a sensor signal 64 to the controller 61 in order to determine variations in the abutment pressure. As indicated above in perfect isolation the sensor 62 will determine stable steady state conditions. In such circumstances there will be no unexpected vibration transmitted to the sensor 62 and therefore the sensor signal 64 sent to the controller 61 will indicate acceptable abutment pressure conditions provided between the elements 20, 21. If there is a deviation from the steady state conditions then the sensor 62 will forward a sensor signal 64 indicating that deviation. The deviation will be assessed by the controller 61 in terms of necessary action in order to return the vibration test arrangement to steady state conditions. In such circumstances an actuation signal 65 will be sent as a control signal to the drive mechanism 63. The drive mechanism 63 may be an electric motor or a stepping motor in order to cause displacement of the elements 20, 21 or more particularly relative displacement as illustrated through the arms 15, 16 in order to alter the abutment pressure presented to the component 12. In such circumstances consistency of abutment pressure can be achieved improving vibration test results. The abutment pressure or force applied by the isolator elements 20, 21 in such circumstances can be set dynamically for retention of test conditions over a whole test cycle.

By aspects of the present invention it will be appreciated that a vibration test arrangement and more particularly an isolation device arrangement is provided which allows additional control of the mode of vibration. Through achieving consistency of abutment pressure through a whole vibration test cycle it will be understood that improved results will be achieved. The dynamic adjustment of the abutment pressure to maintain a steady state through displacement and the clamp association as described above ensures consistence of testing of the mode of vibration of interest. Through use of the control regime comprising the sensor 62, the controller 61 and the drive mechanism 63 a steady state condition in terms of applied abutment pressure upon the node line 13 is achieved. It will also be understood that the controller 61 in association with the sensor 62 can act as a shut down monitor arrangement for a vibration test arrangement in accordance with aspects of the present invention. It will be understood that if the expected test conditions or characteristics are exceeded there will generally be little point in continuing with the test procedure as the results will be unreliable. In such circumstances the controller 61 can ensure that the test conditions are maintained and therefore the validity of the test is achieved.

Through use of the sensor 62 in association with a controller and adjustment of the clamp association 18 it will be understood that the wear upon the isolator elements 20, 21 can be accommodated in order to maintain the same level of abutment pressure.

In basic terms the sensor 62 provides a sensor signal 64 as indicated which either actively determines the conditions at the sensor 62 or normally provides a reference signal consistent with the desired necessary steady state conditions for normal test operations. If these conditions are exceeded then the sensor signal 64 will not correspond with the desired reference signal as determined by the controller 61 and therefore the controller 61 can shut down vibration testing operations or as indicated in accordance with aspects of the present invention adjust through the displacement mechanism 60 the clamp association 18 to alter the abutment pressure and therefore the test conditions in order to return to that desired steady state. In such circumstances the controller 61 typically has an objective of achieving dynamic control to maintain and monitor a steady state condition in terms of vibration testing upon the component 12.

Modifications and alterations to aspects of the present invention will be appreciated by those skilled in the art. For example, more than one sensor may be utilised with regard to altering the abutment pressure between the isolation members. Separate displacement mechanisms may be provided for each isolation member although typically co-ordinated by a single controller or control mechanism to define the abutment pressure.

The vibration testing and isolation device may be used for testing of any type of aerofoil e.g. fan blades, compressor blades or turbine blades of gas turbine engines.

The component to be tested is held in a fixture, more particularly one end of the component is held in the fixture, and in the case of an aerofoil, e.g. a fan blade, a compressor blade or a turbine blade, the root of the blade is held in the fixture. The component is vibrated using any suitable means of producing vibration, for example a device to produce high velocity gas, or air, jets which are directed onto the aerofoil or a shaker device such as an electrodynamic, piezoelectric or magnetostrictive actuator. The component is tested by vibration for fatigue testing or high cycle fatigue testing.

The invention claimed is:

1. A vibration test arrangement for a component, the arrangement comprising:
   means for holding a first end of the component while a second end of the component is unrestrained and free to vibrate;
   means for vibrating the component; and
   an isolation device arranged to engage the component upon a node line of a mode of vibration to isolate a mode of vibration of interest,
   the isolation device having a first isolation member and a second isolation member, the first isolation member and the second isolation member mounted with a clamp association to provide an isolation abutment pressure between the first isolation member and the second isolation member,
   the clamp association comprising a displacement mechanism to provide relative displacement between the first isolation member and the second isolation member, and
   the displacement mechanism being associated with a controller and the controller being associated with a sensor to determine the isolation abutment pressure, the sensor providing signals to the displacement mechanism to alter the isolation abutment pressure.

2. An arrangement as claimed in claim 1 wherein the displacement mechanism comprises a motor associated with the first isolation member and the second isolation member through a cam and/or gear.

3. An arrangement as claimed in claim 1 wherein the clamp association presents the first isolation member and the second isolation member substantially aligned with each other.

4. An arrangement as claimed in claim 1 wherein the displacement mechanism is arranged to provide displacement along a common axis between the first isolation member and the second isolation member.

5. An arrangement as claimed in claim 1 wherein the clamp association includes a spring.

6. An arrangement as claimed in claim 5, wherein
   the first isolation member is provided on a first arm and the second isolation member is provided on a second arm,
   the first arm and the second arm are arranged on a post, and
   the spring is associated with the post.

7. An arrangement as claimed in claim 1 wherein one or each of the isolation members is provided in an aperture, the aperture configured to allow lateral movement relative to an axis between the isolation members.

8. An arrangement a claimed in claim 7 wherein the aperture has a size greater than the isolation member.

9. An arrangement as claimed in claim 7 wherein the aperture is formed from material arranged to allow deformation of the aperture about the isolation member.

10. An arrangement as claimed in claim 1 wherein the first isolation member is provided on a first arm and the second isolation member is provided on a second arm.

11. An arrangement as claimed in claim 10 wherein the first arm and the second arm are arranged on a post.

12. An arrangement as claimed in claim 11 wherein the first arm and the second arm are arranged on the same post.

13. An arrangement as claimed in claim 11 wherein the clamp association is arranged on the post.

14. An arrangement as claimed in claim 11 wherein a guide post is provided to ensure retention of orientation of the arms.

15. An arrangement as claimed in claim 10 wherein the first arm and the second arm are substantially parallel to each other.

16. An arrangement as claimed in claim 1 wherein the isolation abutment pressure is arranged to be sufficient to clamp the component.

17. An arrangement as claimed in claim 16 wherein the component is an aerofoil.

18. An arrangement as claimed in claim 17 wherein the aerofoil is part of a gas turbine engine compressor blade or a part of a gas turbine engine fan blade.

19. A vibration test arrangement for a component, the arrangement comprising:
   a fixture to hold a first end of the component while a second end of the component is unrestrained and free to vibrate;
   a vibrator to vibrate the component; and
   an isolation device arranged to engage the component upon a node line of a mode of vibration to isolate a mode of vibration of interest,
   the isolation device having a first isolation member and a second isolation member, the first isolation member and the second isolation member mounted with a clamp association to provide an isolation abutment pressure between the first isolation member and the second isolation member,
   the clamp association comprising a displacement mechanism to provide relative displacement between the first isolation member and the second isolation member, and
   the displacement mechanism being associated with a controller and the controller being associated with a sensor to determine the isolation abutment pressure, the sensor providing signals to the displacement mechanism to alter the isolation abutment pressure.

* * * * *